(12) United States Patent
Himeno

(10) Patent No.: US 12,400,131 B2
(45) Date of Patent: Aug. 26, 2025

(54) KNOWLEDGE MANAGEMENT SYSTEM

(71) Applicant: IRYOU JYOUHOU GIJYUTU KENKYUSHO CORPORATION, Fukuoka (JP)

(72) Inventor: Shinkichi Himeno, Fukuoka (JP)

(73) Assignee: IRYOU JYOUHOU GIJYUTU KENKYUSHO CORPORATION, Fukuoka (JP)

( * ) Notice: Subject to any disclaimer, the term of this patent is extended or adjusted under 35 U.S.C. 154(b) by 981 days.

(21) Appl. No.: 17/506,084

(22) Filed: Oct. 20, 2021

(65) Prior Publication Data

US 2022/0198285 A1     Jun. 23, 2022

Related U.S. Application Data

(63) Continuation-in-part of application No. PCT/JP2020/020433, filed on May 24, 2020.

(30) Foreign Application Priority Data

May 26, 2019   (JP) ................................ 2019-098163
Nov. 18, 2019  (JP) ................................ 2019-207571

(51) Int. Cl.
   *G06N 5/022*    (2023.01)
   *G06F 16/31*    (2019.01)
   *G06F 16/355*   (2025.01)

(52) U.S. Cl.
   CPC ........... *G06N 5/022* (2013.01); *G06F 16/322* (2019.01); *G06F 16/355* (2019.01)

(58) Field of Classification Search
   CPC ...... G06N 5/022; G06F 16/322; G06F 16/355
   (Continued)

(56) References Cited

U.S. PATENT DOCUMENTS

5,696,885 A * 12/1997 Hekmatpour ......... G06F 3/0481
                                                   706/59
7,827,125 B1    11/2010 Rennison
(Continued)

FOREIGN PATENT DOCUMENTS

EP    3 153 974 A1     4/2017
JP    H09-179739 A     7/1997
(Continued)

OTHER PUBLICATIONS

Search Report issued on Jul. 1, 2022 in corresponding European Application No. 20813236.5; 8 pages.
(Continued)

*Primary Examiner* — Giovanna B Colan
(74) *Attorney, Agent, or Firm* — Maier & Maier, PLLC

(57) ABSTRACT

A knowledge management system includes a knowledge entry management configured to manage at least one knowledge entry in recording or managing knowledge, a knowledge entry attribute description management configured to record and manage an attribute description about the at least one knowledge entry. A term used in the attribute description is another knowledge entry or an attribute description of the other knowledge entry and a reference link to the other knowledge entry or the attribute description of the other knowledge entry is available, and a reference term-using document creation configured to create a document in which the knowledge entry is used as a term and that holds a reference link to the knowledge entry.

12 Claims, 12 Drawing Sheets

(58) Field of Classification Search
USPC .......................... 707/603, 794, 769; 706/50
See application file for complete search history.

(56) References Cited

U.S. PATENT DOCUMENTS

| | | | |
|---|---|---|---|
| 10,831,811 B2* | 11/2020 | Kraus | G06F 16/3346 |
| 2007/0033261 A1 | 2/2007 | Wagner et al. | |
| 2010/0070448 A1* | 3/2010 | Omoigui | H10F 39/1825 |
| | | | 706/55 |
| 2011/0246501 A1* | 10/2011 | McMenamin | G16B 50/00 |
| | | | 707/769 |
| 2012/0072387 A1* | 3/2012 | Yanase | G06F 16/907 |
| | | | 706/50 |
| 2017/0344886 A1* | 11/2017 | Tong | G06N 5/022 |
| 2018/0218786 A1 | 8/2018 | Himeno | |
| 2020/0320405 A1* | 10/2020 | Himeno | G06N 5/02 |

FOREIGN PATENT DOCUMENTS

| | | |
|---|---|---|
| JP | 2005-084754 A | 3/2005 |
| JP | 2012-119004 A | 6/2012 |
| JP | 2019-101517 A | 6/2019 |
| WO | 02/26014 A2 | 4/2002 |

OTHER PUBLICATIONS

International Search Report issued on Jul. 14, 2020 in corresponding International application No. PCT/JP2020/020433; 4 pages.
Kazuhiko Ohe, Ontology Representation and Utilization of Clinical Medical Knowledge; http://www.sanken.osaka-u.ac.ip/labs/nano/contents/meeting/pdf/S12_ohe.pdf; Summary of Invention; 4 pages.
First Office Action issued on Mar. 17, 2020 in corresponding Japanese application No. 2019-207571; 19 pages.
Decision of Refusal issued on Oct. 20, 2020 in corresponding Japanese application No. 2019-207571; 8 pages.
Office Action after Decision of Refusal issued on Apr. 7, 2021 in corresponding Japanese application No. 2019-207571; 14 pages.
Trial and Appeal Decision issued on Jul. 12, 2021 in corresponding Japanese application No. 2019-207571; 17 pages.
Office Action issued Jun. 17, 2024, in corresponding European Application No. 20 813 236.5, 8 pages.

* cited by examiner

Fig 3
TREE STRUCTURE OF KNOWLEDGE "DISEASE NAME"
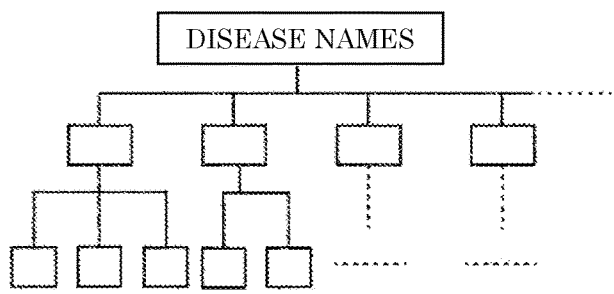
TREE STRUCTURE OF KNOWLEDGE "SYMPTOMS/FINDINGS"
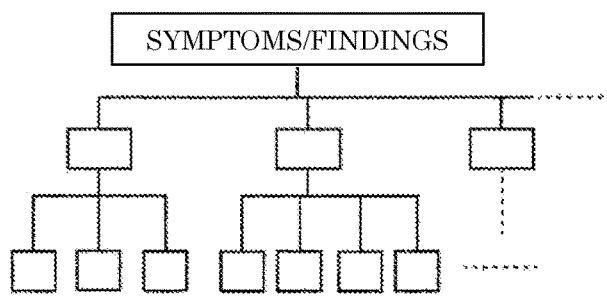
TREE STRUCTURE OF KNOWLEDGE "DRUG"
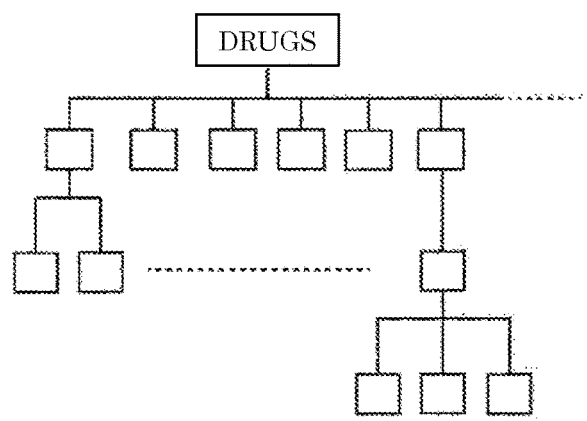

Fig 4

GROUPS OF TREE STRUCTURES OF KNOWLEDGE MANAGEMENT MEANS

| TREE STRUCTURE OF KNOWLEDGE ID | TREE STRUCTURE OF KNOWLEDGE NAME |
|---|---|
| 1 | DISEASE NAME |
| 2 | SYMPTOMS/FINDINGS |
| 3 | DRUG |
| 4 | TREATMENT |
| ⋮ | ⋮ |

Fig 6

KNOWLEDGE ENTRY MANAGEMENT MEANS

| TREE STRUCTURE OF KNOWLEDGE ID | KNOWLEDGE ENTRY ID | KNOWLEDGE ENTRY NAME |
|---|---|---|
| 1 | 1 | DISEASE NAME |
| 1 | 2 | METABOLIC SYSTEM |
| 1 | 3 | DIGESTIVE SYSTEM |
| 1 | 4 | LOCOMOTORIUM SYSTEM |
| 1 | 5 | CIRCULATORY SYSTEM |
| ⋮ | ⋮ | ⋮ |

Fig 8

EXAMPLE OF KNOWLEDGE ENTRY ATTRIBUTE
CATEGORY MANAGEMENT MEANS

| TREE STRUCTURE OF KNOWLEDGE ID | KNOWLEDGE ENTRY ATTRIBUTE CATEGORY ID | KNOWLEDGE ENTRY ATTRIBUTE CATEGORY NAME |
|---|---|---|
| 1 | 1 | ETIOLOGY |
| 1 | 2 | DISEASE STATE |
| 1 | 3 | SYMPTOMS |
| 1 | 4 | TEST FINDINGS |
| 1 | 5 | TREATMENT |
| 1 | 6 | CASE |
| 1 | 7 | LITERATURE |
| ⋮ | ⋮ | ⋮ |

Fig 9 ( a ) REFERENCE LINK
LABEL "HYPERGLYCEMIA" AND LINK TO KNOWLEDGE ENTRY "HYPERGLYCEMIA"
IN TREE STRUCTURE OF KNOWLEDGE "SYMPTOMS/FINDINGS"
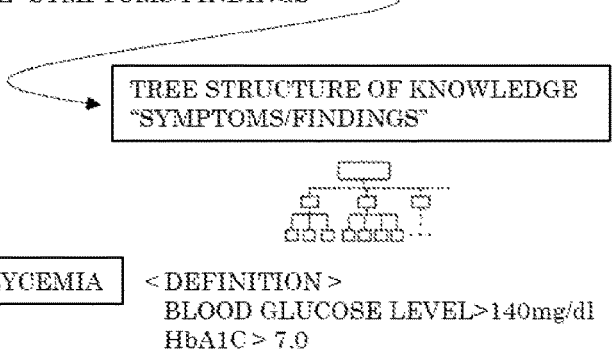
HYPERGLYCEMIA   < DEFINITION >
    BLOOD GLUCOSE LEVEL>140mg/dl
    HbA1C > 7.0
Fig 9 ( b ) TREE STRUCTURE OF KNOWLEDGE "DRUGS"
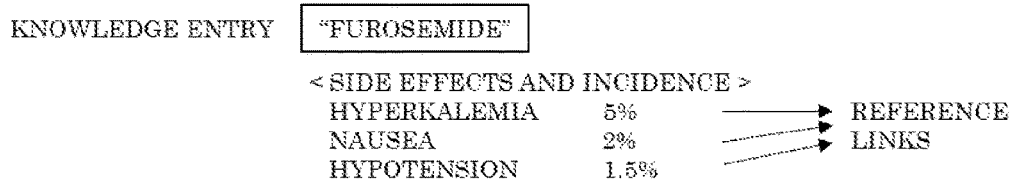
Fig 9 ( c ) DISK HERNIATION
PRE-CHECK SCRIPT FOR MRI SCAN
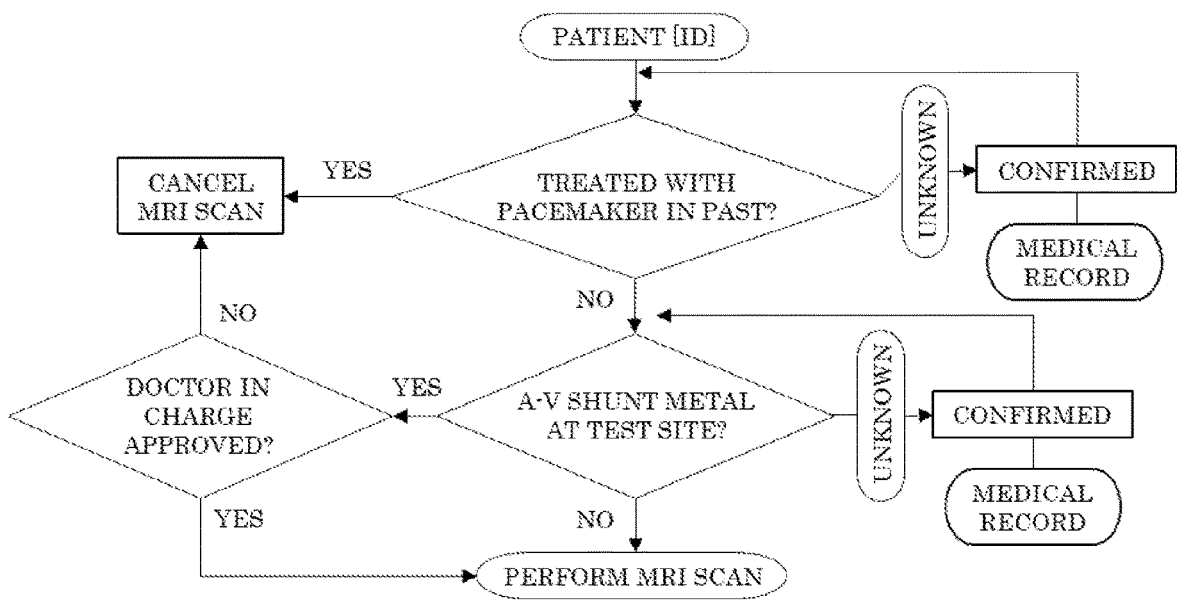

Fig 11

NAME SPACE MANAGEMENT MEANS

| NAME SPACE ID | NAME SPACE NAME |
|---|---|
| 1 | MEDICAL CARE |
| 2 | ART |
| 3 | INDUSTRY |
| 4 | ⋮ |
| ⋮ | |

KNOWLEDGE MANAGEMENT SYSTEM

FIELD

The present invention relates to a knowledge management system that efficiently accumulates and searches for knowledge required to perform inference, decision, recognition, or the like.

BACKGROUND

If a computer can be caused to perform decision or inference routinely performed by persons, routine work can be processed in a large amount and at high speed or simplified. Systems for that purpose have been developed.

Initially, expert systems were developed that previously stores decision rules, such as "if A, then B" and "if B, then C," and, when a proposition "D is A" is given, sequentially apply the previously stored decision rules and infer that "D is C." There is known "MYCIN," which infers an antibiotic most suitable for an infectious disease.

More flexible search has been needed since the entry into the Internet era. Such search is, for example, to answer a question "E is musician?" using records or declarations on the Web, such as "E is violinist," "violinist is musician," and "conductor is musician" (Semantic Web).

Here, subordinate concepts, such as "violinist," "conductor," and "composer," are developed under a superordinate concept "musician." By describing the concepts structurally (ontology) as described above, it can be inferred that "E is violinist and therefore is also musician" even if there is no direct description "E is musician" on the Web. That is, the question can be answered correctly.

In this case, it is necessary to previously describe individual concepts or relations in a unified style using a format, such as XML, so that concepts in many fields can be searched for interdisciplinarily. As one example of the unified style, the Resource Description Framework (RDF) is proposed. The RDF's way of describing a concept or relation for each piece is compatible with program languages, such as Prolog, and easily adapts itself to relational databases.

The medical field has also attempted to construct disease ontologies as shown in Non-Patent Literature 1 below. The general industrial field has also proposed Patent Literature 1 and the like.

PATENT LITERATURE

Patent Literature 1: Japanese Unexamined Patent Application Publication No. 2012-119004

NON-PATENT LITERATURE

Non-Patent Literature 1: Ontology Representation and Utilization of Clinical Medical Knowledge (http://www.sanken.osaka-u.ac.jp/labs/nano/contents/meeting/pdf/S12_ohe.pdf)

SUMMARY

Initial expert systems had the hard work of storing a large number of decision rules required for practical-level operation. Also, the condition portion A of "if A, then B" is applied only to a description that precisely matches the condition portion A. Accordingly, if "musician" with respect to "violinist" is searched for, as is done in the above example, there would be no matching description.

Semantic Web has become able to support somewhat fuzzy search using a kind of common sense that "violinist," "conductor", "composer," and the like are also included in the subordinate concept "musician," on the basis of a structural description, such as an ontology.

However, when a specific ontology is actually constructed, the same content can be described in multiple manners and the described structure fluctuates among constructors. This is because the degree of freedom of the description format is excessively high.

Thus, the same information is often described in different styles. In this case, when multiple persons construct multiple ontologies as parallel work, confusion would occur due to the mismatch between the description styles.

Also, since various description styles are mixed, a developed ontology is not easily visually comprehensible in many cases and is often poor in readability.

Even if individual knowledge pieces, such as knowledge areas, knowledge items, attribute descriptions, and parent-child relationship descriptions, are described in a format, such as RDF, similar fluctuations in the description style are unavoidable. An ontology is originally an enumeration of a large amount of knowledge pieces, has difficulty in providing an overview of the knowledge, and is extremely poor in readability.

To efficiently describe a large amount of knowledge, it is necessary not only to describe the knowledge in a computer-understandable format but also to provide readability such that persons can also easily understand the description.

Allowing a user to easily describe knowledge without special knowledge or skills and allowing the user to easily point out a contradiction or the like when seeing the description are characteristics essential for many persons having knowledge in certain fields but not being an expert about a computer to construct ontologies or the like in parallel while cooperating with each other through the Web, as recommended in WEB2.0. Also, creating a document supported by knowledge descriptions as described above is useful to facilitate a correct understanding.

The present invention has been made to solve the above background art problems, and an object thereof is to allow a user to create a document supported by knowledge descriptions by including knowledge entry management means configured to manage at least one knowledge entry in recording and managing knowledge, knowledge entry attribute description management means configured to record and manage an attribute description about the at least one knowledge entry, wherein a term used in the attribute description is another knowledge entry or an attribute description of the other knowledge entry defining or describing the term and wherein a reference link to the other knowledge entry or the attribute description of the other knowledge entry is available, and reference term-using document creation means configured to create a document in which the knowledge entry managed by the knowledge entry attribute description management means is used as a term and that holds a reference link to the knowledge entry. Another object is to allow a user to systemically describe knowledge without fluctuations in the description by clearly classifying and organizing knowledge in a certain area into multiple tree structures of knowledge, wherein, in each tree structure of knowledge, knowledge entries forming the tree are developed in a parent-child relationship hierarchical structure, wherein each knowledge entry is an aggregate of entry attribute descriptions about the knowledge entry, and wherein each entry attribute description includes a term (reference term) defined by another knowledge entry or entry attribute description and a reference link to the term.

Another object is to inherit the entry attribute descriptions of a parent knowledge entry as entry attribute descriptions of a child knowledge entry and thus to eliminate the need to describe the attribute descriptions in an overlapping manner.

Another object is to allow a user to concentrate on the field of interest without having to worry about overlaps with tree structure of knowledge names or knowledge entry names in another field by allowing the user to manage tree structure of knowledge in the other field as different independent tree-structure-of-knowledge group separated by name spaces.

Another object is to, by establishing such a knowledge management framework, allow a user to construct a knowledge management system that provides good readability not only allowing for machine processing but also allowing persons to understand information at a glance and that prevents fluctuations in the description even if anyone creates a document and thus to provide a knowledge processing infrastructure that allows for flexible, high-level search or inference.

Another object is to allow a user to reconfigure a knowledge management system by extracting and integrating part or all of the above-mentioned knowledge management system into another knowledge management system and thus to allow the user to flexibly operate the knowledge management system.

Another object is to allow a user to not only view information in the constructed knowledge management system but also effectively utilize the knowledge management system in the real society by allowing the knowledge management system to receive an inquiry and respond to the inquiry. Another object is to ensure security against destruction or confusion by managing the user-specific performance authorities and setting the search scope.

To accomplish the above objects, a knowledge management system includes knowledge entry management means configured to manage at least one knowledge entry in recording and managing knowledge, knowledge entry attribute description management means configured to record and manage an attribute description about the at least one knowledge entry, wherein a term used in the attribute description is another knowledge entry or an attribute description of the other knowledge entry defining or describing the term and wherein a reference link to the other knowledge entry or the attribute description of the other knowledge entry is available, and reference term-using document creation means configured to create a document in which the knowledge entry managed by the knowledge entry attribute description management means is used as a term and that holds a reference link to the knowledge entry.

According to the knowledge management system, the knowledge management system includes knowledge entry attribute category management means configured to manage the knowledge entry attribute description such that the knowledge entry attribute description is classified into a category.

According to the knowledge management system, the knowledge management system includes tree-structure-of-knowledge group management means configured to manage at least one tree structure of knowledge, knowledge entry management means configured to manage at least one knowledge entry present in each of the at least one tree structure of knowledge, wherein each of the at least one knowledge entry includes a knowledge entry attribute description describing an attribute about the knowledge entry and a knowledge entry parent-child relationship link describing a parent-child relationship with another knowledge entry of the at least one tree structure of knowledge, and tree-shaped knowledge management means in which the knowledge entry attribute description includes a term defined by a knowledge entry belonging to a different or identical tree structure of knowledge or an entry attribute description of the knowledge entry, and a reference link to the term.

According to the knowledge management system, the knowledge management system includes knowledge entry attribute description inheritance means configured to inherit an entry attribute description of a parent knowledge entry as an entry attribute description of a child knowledge entry in the parent-child relationship.

According to the knowledge management system, the knowledge management system includes reference characteristics management means configured to manage a script to be executed when making reference.

According to the knowledge management system, in the knowledge management system, the reference characteristics management means is configured to be able to change strength of the reference in accordance with an observation frequency.

According to the knowledge management system, the knowledge management system includes external document reference means configured to refer to an external document related to an entry attribute description.

According to the knowledge management system, the knowledge management system includes name space management means configured to manage the at least one tree structure of knowledge such that the at least one tree structure of knowledge is classified into a name space.

According to the knowledge management system, the knowledge management system includes knowledge export means configured to create a knowledge management subset by extracting any portions of a name space, a tree structure of knowledge, a knowledge entry, an entry attribute description, and a parent-child relationship link and to export the knowledge management subset to another knowledge management system.

According to the knowledge management system, the knowledge management system includes knowledge import means configured to import the knowledge management subset extracted by the knowledge export means or a knowledge management subset from a separately constructed knowledge management system and to reconfigure a name space, a tree structure of knowledge, a knowledge entry, an entry attribute description, and a parent-child relationship link.

According to the knowledge management system, the knowledge management system includes user authority management means configured to manage user-specific authorities to perform functions of creating, editing, deleting, and referring to the name space, the tree structure of knowledge, the knowledge entry, the knowledge entry attribute category, the knowledge entry attribute description, and the parent-child relationship link.

According to the knowledge management system, the knowledge management system includes knowledge view means configured to allow a user to view the parent-child relationship between the at least one knowledge entry and the other knowledge entry or the knowledge attribute description of the at least one knowledge entry.

According to the knowledge management system, the knowledge management system includes knowledge inquiry receiving means configured to receive an inquiry about recorded or managed information and knowledge inquiry response means configured to respond to the inquiry.

According to the knowledge management system, the knowledge management system includes search scope management means configured to manage users who have created the name space, the tree structure of knowledge, the knowledge entry, the entry attribute description, and the parent-child relationship link and to exclude a portion of a knowledge management system created by a specific user or user group from a search target range of the view or the knowledge inquiry or conversely handle only a portion of a knowledge management system created by a specific user or user group as the search target range of the view or the knowledge inquiry.

Advantageous Effects of Invention

The knowledge management system includes the knowledge entry management means and thus manages at least one knowledge entry.

The knowledge management system includes the knowledge entry attribute description management means and thus records and manages an attribute description about the at least one knowledge entry.

A term used in the attribute description is another knowledge entry or an attribute description of the other knowledge entry defining or describing the term, and a reference link to the other knowledge entry or the attribute description of the other knowledge entry is available.

The knowledge management system includes the reference term-using document creation means and thus creates a document in which the knowledge entry managed by the knowledge entry attribute description management means is used as a term and that holds a reference link to the knowledge entry.

The knowledge management system includes the reference term-using document creation means and thus create a document in which the knowledge entry managed by the knowledge entry attribute description management means is used as a term and that holds a reference link to the knowledge entry.

The knowledge management system includes the knowledge entry attribute category management means and thus manages the knowledge entry attribute description such that the knowledge entry attribute description is classified into a category.

The knowledge management system includes the knowledge entry management means and thus manages the tree-structure-of-knowledge group management means configured to manage at least one tree structure of knowledge, and at least one knowledge entry present in each of the at least one tree structure of knowledge.

The knowledge management system includes the knowledge entry parent-child relationship link and thus describes a knowledge entry attribute description describing an attribute about the knowledge entry, and a parent-child relationship with another knowledge entry of the at least one tree structure of knowledge.

Tree-shaped knowledge management means includes a term defined by a knowledge entry belonging to a different or identical tree structure of knowledge or an entry attribute description of the knowledge entry, and a reference link to the term.

The knowledge management system includes the knowledge entry attribute description inheritance means and thus inherits an entry attribute description of a parent knowledge entry as an entry attribute description of a child knowledge entry in the parent-child relationship.

The knowledge management system includes the reference characteristics management means and thus manages a script to be executed when making reference.

In the knowledge management system, the reference characteristics management means is configured to be able to change strength of the reference in accordance with an observation frequency.

The knowledge management system includes the external document reference means and thus refers to an external document related to an entry attribute description.

The knowledge management system includes the name space management means and thus manages the at least one tree structure of knowledge such that the at least one tree structure of knowledge is classified into a name space.

The knowledge management system includes the knowledge export means and thus creates a knowledge management subset by extracting any portions of a name space, a tree structure of knowledge, a knowledge entry, an entry attribute description, and a parent-child relationship link and exports the knowledge management subset to another knowledge management system.

The knowledge management system of includes the knowledge import means and thus imports the knowledge management subset extracted by the knowledge export means or a knowledge management subset from a separately constructed knowledge management system and reconfigures a name space, a tree structure of knowledge, a knowledge entry, an entry attribute description, and a parent-child relationship link.

The knowledge management system includes the user authority management means and thus manages user-specific authorities to perform functions of creating, editing, deleting, and referring to the name space, the tree structure of knowledge, the knowledge entry, the knowledge entry attribute category, the knowledge entry attribute description, and the parent-child relationship link.

The knowledge management system includes the knowledge view means configured to allow a user to view the parent-child relationship between the at least one knowledge entry and the other knowledge entry or the knowledge attribute description of the at least one knowledge entry.

The knowledge management system includes the knowledge inquiry receiving means and thus receives an inquiry about recorded or managed information.

The knowledge management system includes the knowledge inquiry response means and thus responds to the inquiry.

The knowledge management system includes the search scope management means and thus manages users who have created the name space, the tree structure of knowledge, the knowledge entry, the entry attribute description, and the parent-child relationship link and excludes a portion of a knowledge management system created by a specific user or user group from a search target range of the view or the knowledge inquiry or conversely handles only a portion of a knowledge management system created by a specific user or user group as the search target range of the view or the knowledge inquiry.

BRIEF DESCRIPTION OF THE DRAWINGS

FIG. 3 is a schematic view of tree-structure-of-knowledge group, which are an example of tree-structure-of-knowledge group and includes tree structures of knowledge such as disease name, symptoms/findings, and drug.

FIG. 4 is a diagram showing an example of tree-structure-of-knowledge group management means that manages the tree-structure-of-knowledge IDs and tree structure of knowledge names of tree-structure-of-knowledge group tree structures of knowledge in the form of a master table.

FIG. 6 is a diagram showing an example of knowledge entry management means that manages tree-structure-of-knowledge IDs, knowledge entry IDs, and knowledge entry names in the form of a master table with respect to knowledge entries forming the tree structure of knowledge "disease name."

FIG. 8 is a diagram showing an example of knowledge entry attribute category management means that manages tree-structure-of-knowledge IDs, knowledge entry attribute class IDs, and knowledge entry attribute category names in the form of a master table.

FIG. 9(*a*) shows an example of a label and a reference link to a knowledge entry item or a knowledge attribute category "definition" in the knowledge entry item;

FIG. 9(*b*) shows an example of a reference link that manages reference strength such as incidence; and FIG. 9(*c*) shows an example of a reference link that defines a script to be executed when making reference.

FIG. 11 is a diagram showing name space management means.

DESCRIPTION OF EMBODIMENTS

The knowledge management system includes the server apparatus, the database and the terminal. The server apparatus, the database and the terminal connected through network. The server apparatus is a prior computer. The server apparatus includes: an arithmetic apparatus including the processor, a main storage apparatus, an auxiliary storage apparatus, input apparatus, output apparatus, and communication apparatus. The arithmetic apparatus, the main storage apparatus, the auxiliary storage apparatus, input apparatus, output apparatus, the communication apparatus connected through a bus interface. The arithmetic apparatus includes the processor that can execute an instruction set. The main storage apparatus includes a volatile memory such as a random access memory (RAM). The auxiliary storage apparatus includes a recording medium such as a nonvolatile memory, and a recording method thereof is not limited. The recording medium indicates a hard disk drive (HDD) or a solid state drive (SSD), for example. The input apparatus is, for example, a keyboard device. The output apparatus includes, for example, display as a liquid crystal panel. The communication apparatus is a network interface that can connect to network. The processor of the server apparatus executes the function of the units of the knowledge management system including: knowledge entry management means, knowledge entry attribute description management means, reference term-using document creation means, knowledge entry attribute category management means, tree-structure-of-knowledge group management means, knowledge entry management means, tree structure of knowledge management means, knowledge entry attribute description inheritance means, reference characteristics management means, external document reference means, name space management means, knowledge export means, knowledge import means, user authority management means, knowledge view means, knowledge inquiry receiving means, search scope management means or the like. The database is composed of the auxiliary storage apparatus of the server apparatus or the auxiliary storage apparatus independent from the server apparatus. The database stores information managed by the knowledge management system. The terminal is a prior computer including a processor.

The present application is a system that is run using a computer.

This computer includes an input device (mouse, keyboard, etc.), an output device (monitor, printer, etc.), a storage device (memory, hard disk), a computing device (CPU), a controller (CPU), and the like, as well as includes a program for performing the means (functions) of the present application.

Figure 1:
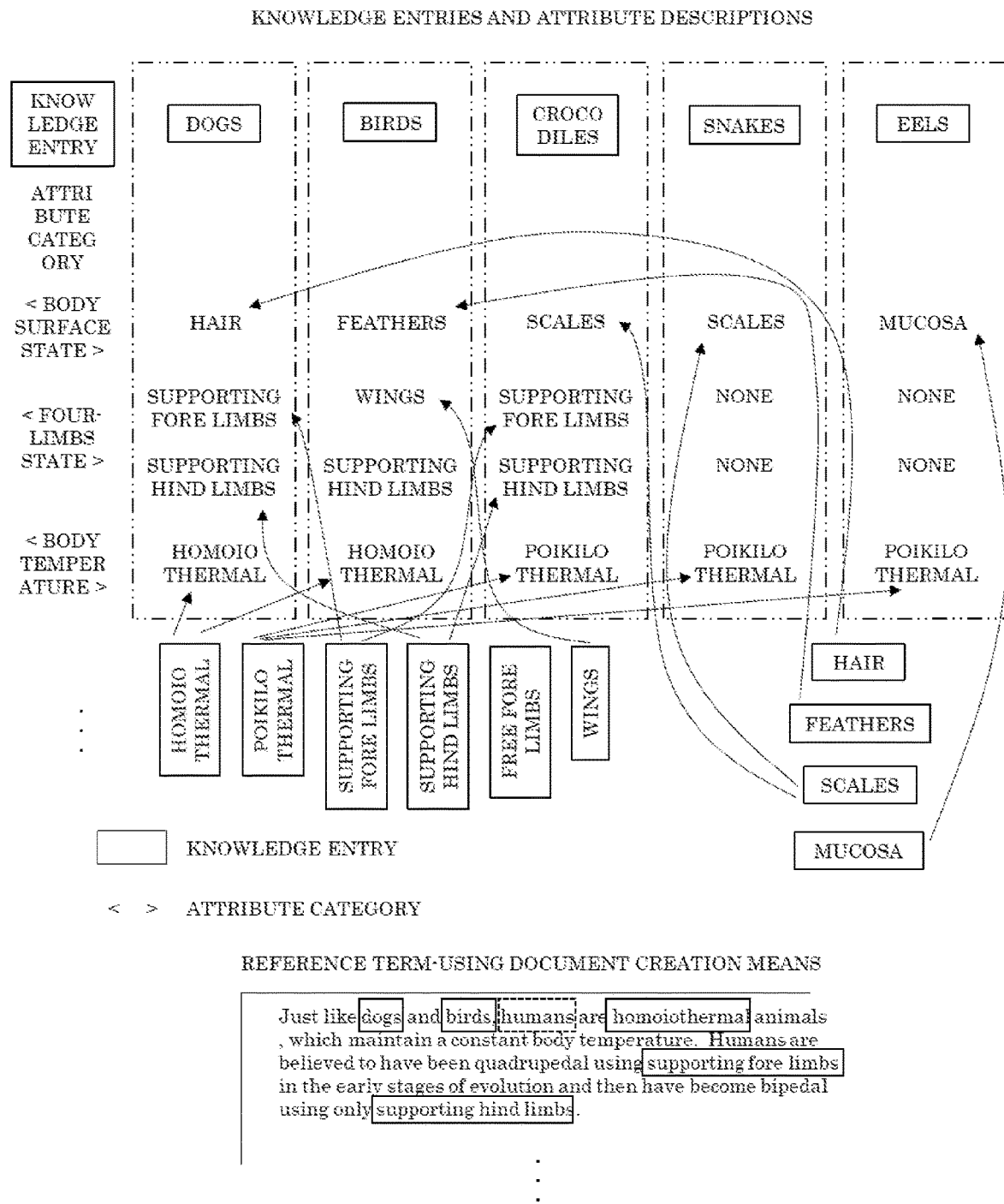
FIG. 1 is a diagram showing knowledge entries and attribute descriptions, and document creation means using those as reference terms.

FIG. 1 is a diagram showing knowledge entries and attribute descriptions, and document creation means using those as reference terms.

Animals are used as examples of knowledge entries (knowledge entry management means).

Each knowledge entry has attribute descriptions (knowledge entry attribute description management means), and the attribute descriptions are classified into attribute categories, such as body surface state, four-limbs state, and body temperature (knowledge entry attribute category management means).

Terms used in the attribute descriptions have reference links to terms defined by other knowledge entries or the attributes of the other knowledge entries (reference terms, reference links).

The reference term-using document creation means creates a document in which knowledge entries managed by the knowledge entry attribute description means are used as terms and that holds reference links to the knowledge entries and thus is able to create a document supported by knowledge descriptions. In an example document of FIG. 1, dogs, birds, homoiothermal, supporting fore limbs, supporting hind limbs, and the like serve as reference terms. As used herein, "humans" has yet to be defined as a term of a knowledge entry managed by the knowledge entry attribute description management means. As seen above, while it is desirable to use reference terms as keywords in a document, self-evident or transiently undefined terms may be used.

The above configuration allows a user to, when an unknown term is present in a document, refer to a knowledge entry or knowledge entry attribute description that defines the term by following the reference link of the term and to deeply understood the term by following a parent-child relationship link (to be discussed later) or the like and thus view a related knowledge entry or knowledge entry attribute description. Also, as shown in FIG. 9, each time a reference term appears in a document, a reference link of this term to a knowledge entry is counted up. Thus, the reference strength is increased and can be used as the basis of Bayesian probability calculation.

The knowledge entry management means, the knowledge entry attribute category management means, and reference link management means are implemented, for example, by creating a master file of the knowledge entries, knowledge entry attribute categories, and reference links, making knowledge entry attribute descriptions using XML or JSON objects or the like, and combining a relational database or the like as necessary.

With respect to the reference links, the names or attribute descriptions of the knowledge entries may be used as a controlled vocabulary (thesaurus) and may be searched for as necessary. On the other hand, search can be speeded up by forming a database as a reference link master file from the referenced terms, reference link sources, reference link destinations, and the like.

In FIG. 1, the knowledge entries are arranged in parallel but in a structureless manner and therefore have extremely poor visibility as a whole.

Also, many attribute descriptions are recognized to overlap each other. Thus, when a change is made to one attribute description, changes have to be made to the other overlapping attribute descriptions. This makes it hard work to maintain the whole consistency. In this case, common attribute descriptions only have to be pulled out using superordinate concepts, such as animals, mammals, reptiles.

Figure 2:
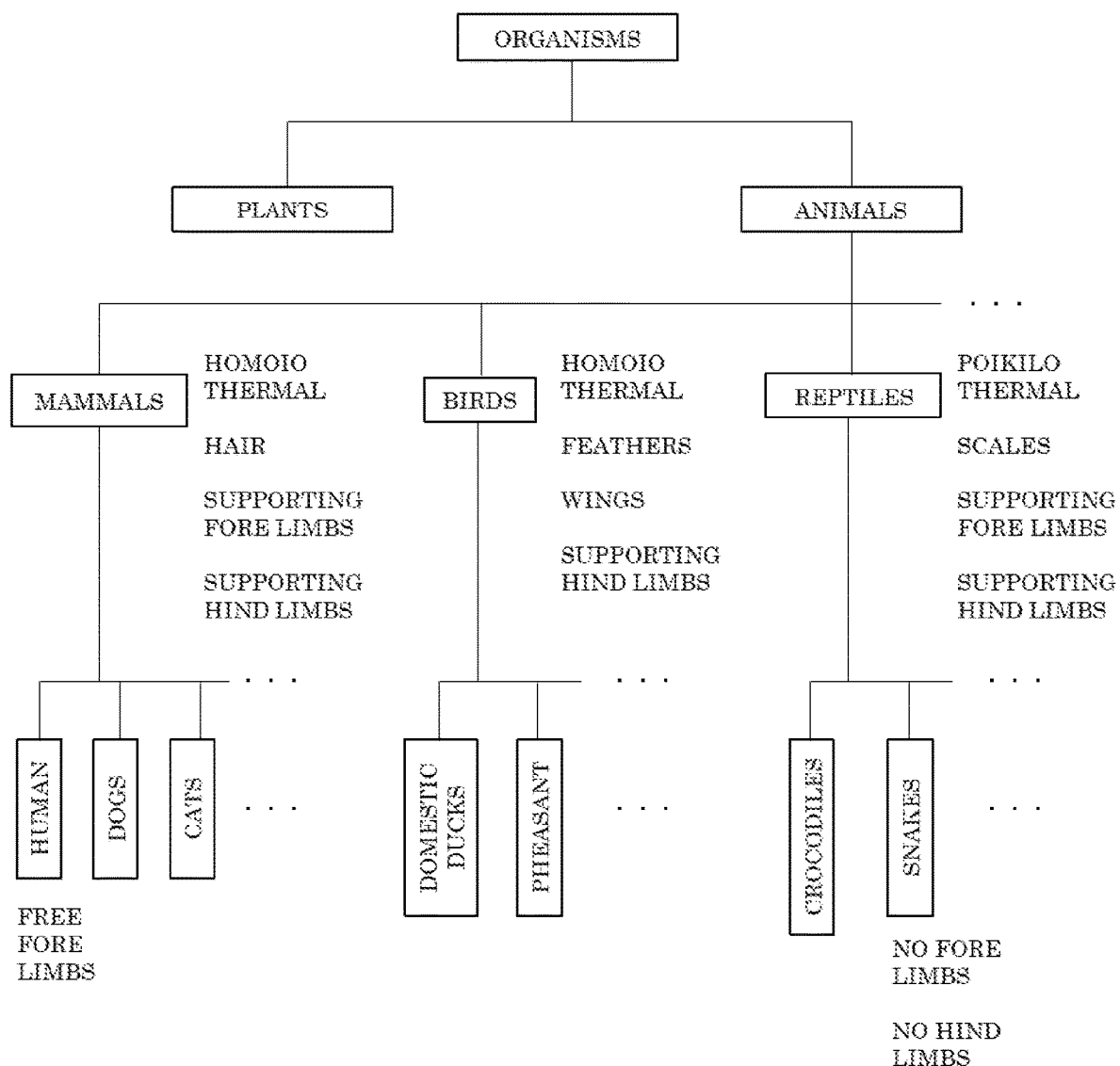
FIG. 2 is a diagram showing tree structure of knowledge management means.

FIG. 2 is a diagram showing tree-shaped knowledge management means.

The tree-shaped knowledge management means reorganizes knowledge entries into a hierarchical structure and pulls out common attribute descriptions of subordinate knowledge entries as the attributes of superordinate knowledge entries so that the same description is made only in one position. When necessary, the attributes of a superordinate knowledge entry are inherited as attributes of a subordinate knowledge entry (knowledge entry attribute description inheritance means).

While the attribute descriptions of a parent may be inherited as the knowledge entry attribute descriptions of a child knowledge entry as they are, the child knowledge entry may have knowledge entry attribute descriptions different from the inherited attribute descriptions. In this case, the attribute descriptions of the child knowledge entry are written over or added to the knowledge entry attribute descriptions inherited from the parent.

The written-over or added attribute descriptions are further inherited to grandson and more subordinate knowledge entries.

A relationship in which a subordinate knowledge entry is included in a superordinate knowledge entry, as is seen in "dog is a mammal," is called the is-a relationship. In this case, the knowledge entry attribute description inheritance means functions.

The dendrogram of organisms is a typical example.

In this relationship, the knowledge entry attribute description inheritance means is meaningful.

On the other hand, consider a tree structure of knowledge in which a "animal" has a "head and neck," "trunk," "two fore limbs," and "two hind limbs" (has-a relationship). In this case, the "head and neck," "trunk," and the like are parts of the body of the "animal" (part-of relationship), and these do not have an inclusion relationship such as the "is-a" relationship.

Accordingly, the knowledge entry attribute description inheritance means does not function.

In this case, the knowledge entries may be formed into a tree structure. This is because it is useful to obtain good visibility by organizing the knowledge entries. If the knowledge entries are small in number, they need not be organized into a tree shape and it is only necessary to provide reference links to the knowledge entries.

As seen above, the knowledge management system of the present invention selectively uses a tree structure of knowledge in which the "is-a" relationship is present and the knowledge entry attribute description inheritance means functions, a tree structure of knowledge in which a relationship other than "is-a" is present and the knowledge entry attribute description inheritance means does not function, and knowledge entries that do not have a tree structure, as the sources of reference links.

While tree structures of knowledge having the "is-a" relationship is mainly handled below with reference to the diagrams, other tree structures of knowledge and single knowledge entries are also included in the present invention as the sources of reference links.

Referring to FIG. 3, the knowledge management system of the present invention will be outlined using medical knowledge as an example.

FIG. 3 shows "disease," "symptoms/test findings," "drug," and the like as examples of tree structures of knowledge.

Other conceivable tree structures of knowledge include "treatment," "insurance claim," and the like.

Each tree structure of knowledge consists of an aggregate of knowledge entries coupled by parent-child relationships.

tree-structure-of-knowledge group management means manages these tree structures of knowledge in the tree-structure-of-knowledge groups.

FIG. 4 shows an example of the tree-structure-of-knowledge group management means. This tree-structure-of-knowledge group management means manages the tree-structure-of-knowledge IDs and tree structure of knowledge names of the tree-structure-of-knowledge group in the form of a master table.

Figure 5:
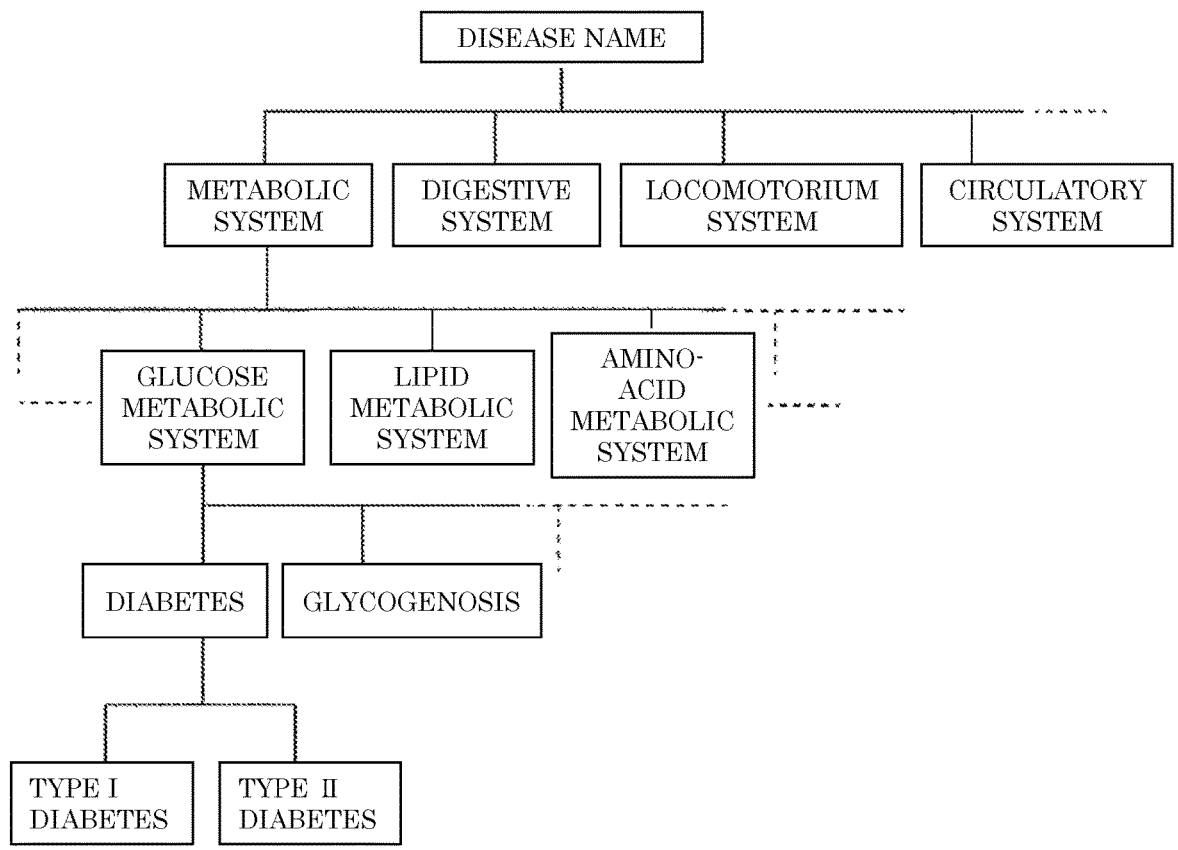
FIG. 5 shows some of knowledge entries forming a tree structure of knowledge "disease name," which is an example of a tree structure of knowledge.

FIG. 5 shows knowledge entries forming a tree structure of knowledge "disease name," which is an example of a tree structure of knowledge.

The knowledge entries of "disease name" are first classified into major categories, such as "metabolic system," "digestive system," "locomotorium system," and "circulatory system." Each major category is classified into medium categories, for example, "metabolic system" is classified into "glucose metabolic system," "lipid metabolic system," "amino-acid metabolic system," and the like. The medium category "glucose metabolic system" is classified into minor categories, such as "diabetes" and "glycogenosis."

The minor category "diabetes" includes "type I diabetes" and "type II diabetes."

"Type I diabetes," "type II diabetes," and the like, which are ends or leaves of the tree structure of knowledge, are specific disease names. By pulling out common attributes of these entries, the knowledge entries, such as the minor categories, medium categories, and major categories, which are branches, are formed. These knowledge entries serve as container-type knowledge entries containing the disease names, which are more subordinate categories, that is, leaves.

While this tree structure of knowledge has a hierarchy consisting of the major, medium, and minor categories, a tree structure of knowledge having a deeper or shallower hierarchy may be formed depending on the field. While the disease state-based classification criterion is used here, the knowledge entries may be classified into "nape," "neck," "upper limbs," and the like on a site basis, or may be classified into "inflammation-based," "tumor-based,"

"infection-based," "heredity-based," and the like on an etiology basis. For this reason, the descriptions fluctuate among classification criteria. However, once the administrator of the knowledge management system determines the classification criterion, the descriptions do not fluctuate from then on. In short, the administrator of the knowledge management system preferably sets the classification criterion in accordance with the purpose. Multiple tree structure of knowledges having different classification criteria may be present in parallel.

FIG. 6 is an example of the knowledge entry management means.

This knowledge entry management means manages the IDs of the knowledge entries in each tree structure of knowledge in the form of a master table.

While each knowledge entry name has to be unique in the tree structure of knowledge to which it belongs to, knowledge entries belonging to different tree structures of knowledge are allowed to have the same name. This is because the tree structures of knowledge are distinguished from each other by the tree-structure-of-knowledge IDs as defined in FIG. 2.

While, in this diagram, the knowledge entries in the group of tree structures of knowledge are centrally managed regardless of which tree structure of knowledge each knowledge entry belongs to, a different master table may be created for each of the tree structures of knowledge so that the knowledge entries are managed in the different master tables.

If the knowledge entry names are unique through the structure-of-knowledge group regardless of which tree structure of knowledge each knowledge entry belongs to, there is no need for the tree structure of knowledge IDs in the first column of FIG. 6.

Figure 7:
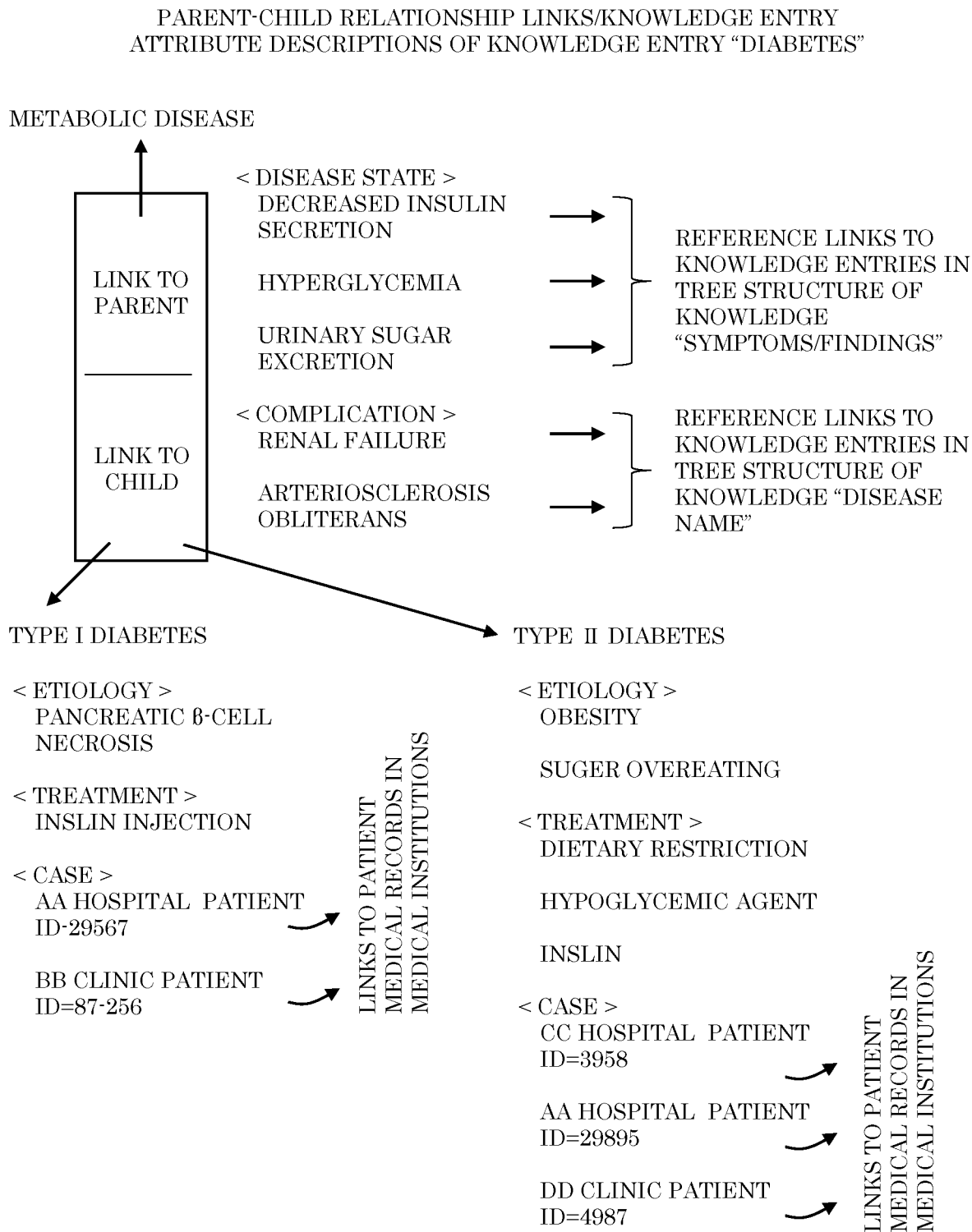
FIG. 7 is a diagram showing parent-child relationship links and knowledge entry attribute descriptions using diabetes, which is one of knowledge entries forming the tree structure of knowledge "disease name," as an example.

FIG. 7 is a diagram showing parent-child relationships and attribute descriptions using, as an example, the knowledge entry "diabetes," which is one of container-type knowledge entries, "type I diabetes" and "type II diabetes," which are leaves thereof.

"Diabetes" has a link to "metabolic system" serving as a parent knowledge entry and links to "type I diabetes" and "type II diabetes" serving as child knowledge entries.

The attribute description categories of "diabetes" include <disease state>, <complication>, and the like.

<Disease state> includes decreased insulin secretion, hyperglycemia, urinary sugar excretion, and the like.

Each <disease state> item has a reference link to a corresponding knowledge entry in the tree structure of knowledge "symptoms/findings," which is another tree structure of knowledge.

This means that the attribute descriptions are made using a controlled vocabulary, as is done in a thesaurus, allowing for suppression of fluctuations in the descriptions.

Of course, the attribute descriptions may be directly made using character strings as is done conventionally, or may be linked to a document. However, those attribute descriptions are not preferable since it is difficult to suppress fluctuations and to utilize the function of reference links (to be discussed later).

<Complication> includes "renal failure," "arteriosclerosis obliterans," and the like. These complications have reference links to corresponding knowledge entries in the same tree structure of knowledge "disease name."

The etiology of "type I diabetes" is the rapid necrosis of the 0 cells of the pancreas and therefore supplementation by insulin injection is only treatment.

On the other hand, the etiology of "type II diabetes" is obesity, overeating of sugar, or the like, and the treatment is dietary restriction and oral administration of hypoglycemic agent and, finally, insulin injection.

As seen above, while "type I diabetes" and "type II diabetes" have different descriptions in <etiology> and <treatment>, they have common descriptions in other items, such as <disease state> and <complication> and therefore the common descriptions are made in the parent knowledge entry "diabetes."

Even if "type I diabetes" and "type II diabetes," which are leaves, have descriptions only in <etiology> and <treatment>, they inherit the attribute descriptions in <disease state> and <complication> of "diabetes," which is a parent knowledge entry, and, further, the attribute descriptions in more superordinate knowledge entries, such as "metabolic disease."

As seen above, the common attribute descriptions are pulled out to the parent knowledge entry and therefore the minimum attribute descriptions only have to be made in the child knowledge entries. While the attribute descriptions of the knowledge entry may be formed in mind by following the respective parent-child relationships, the attribute descriptions are easily comprehensively grasped by using the knowledge entry attribute description inheritance means to inherit and displaying all the attribute descriptions of the knowledge entry serving as the parent of this knowledge entry.

While the attribute descriptions inherited from the parent on a knowledge entry attribute category basis may become the knowledge entry attribute descriptions of the child knowledge entry as they are, the child knowledge entry may have knowledge entry attribute descriptions different from the attribute descriptions inherited to the knowledge entry attribute categories thereof. In this case, the knowledge entry attribute descriptions of the child knowledge entry are written over or added to the knowledge entry attribute descriptions inherited from the parent. The written-over or added attribute descriptions are further inherited to the grandson and more subordinate knowledge entries.

A user may selectively use writing-over or addition using the knowledge entry attribute description inheritance means as necessary.

While attribute descriptions may be made without using attribute categories, use of attribute categories allows a user to easily grasp attribute category-based inheritance using the knowledge entry attribute description inheritance means. Also, use of attribute categories is more useful, since it can facilitate writing-over or addition of attribute descriptions.

A knowledge entry attribute category <case> is recording reference links to the medical records of cases with this disease name.

Thus, the records of patients with this disease can be directly referred to. The reference links to the medical records of the cases may be in any form, such as medical institution ID+patient ID, URL of patient medical record, and file name of patient medical record, as long as they can provide access to case information. The reference links may further include the document IDs of the patient medical records, such as document type+creation year/month/day. Also, a knowledge entry attribute category, such as <literature>, may be provided so that links to related books or files, or documents on the Web may be described (external document reference means).

FIG. 8 is an example of the knowledge entry attribute category management means.

This knowledge entry attribute category management means manages the IDs of the knowledge entry attribute categories in the tree-structure-of-knowledge group in the form of a master table.

While each knowledge entry attribute category name has to be unique in the tree structure of knowledge to which it belongs to, knowledge entry attribute categories belonging to different tree structures of knowledge are allowed to have the same name since the tree structures of knowledge are distinguished from each other by the tree-structure-of-knowledge IDs.

While, in this diagram, the knowledge entry attribute categories in the tree-structure-of-knowledge group are centrally managed regardless of which tree structure of knowledge each knowledge entry attribute category belongs to, a different master table may be created for each tree structure of knowledge so that the knowledge entry attribute categories are managed in the different master tables.

If unique knowledge entry attribute category names are used in the tree-structure-of-knowledge group, the tree-structure-of-knowledge IDs in the first column are not required. Also, a method of directly writing knowledge entry attribute categories into knowledge entries forming the route of each tree structure of knowledge such that the attribute categories are inherited to subordinates may be used without using the knowledge entry attribute category management means as described with reference to this diagram. However, the procedure becomes complicated compared to that in the master table type when automating search or the like. For this reason, this method is not preferable, particularly, in a large knowledge management system. While a user may feely define knowledge entry attribute categories in each knowledge entry, this approach is more likely to cause overlaps, or fluctuations in the descriptions and is not preferable as well.

FIG. 9 shows various embodiments of reference links.

FIG. 9(a) shows an example of the structure of the reference link of "hyperglycemia" in <disease state> of "diabetes" in FIG. 7.

The reference link consists of a label "hyperglycemia" and a link to a knowledge entry "hyperglycemia" in the tree structure of knowledge "symptoms/findings."

The label may be linked to a knowledge entry attribute category <definition> in "hyperglycemia." The label is viewed display information.

While the knowledge entry name of the link destination may be directly used as the label as in this example, "hyperglycemia, blood sugar level>140 mg/dl" or the like may be used for visibility.

Thus, even if there is no step of individually referring to the link destination, a summary can be easily grasped at a glance.

FIG. 9(b) shows reference links in a knowledge entry attribute category <side effects/incidence> in a knowledge entry "furosemide" in the tree structure of knowledge "drug."

The first row consists of a label "hyperkalemia," a reference strength of "5%," and a reference link to a knowledge entry "hyperkalemia" in the tree structure of knowledge "symptoms/findings."

Even if there are various side effects, the incidences thereof are not uniform. By providing incidence information as the reference strength, the order of precedence of side effects to be considered is clarified.

The incidence here serves as a priori probability in Bayesian probability. When side effects occur under multiple-drug administration, the incidence is useful in performing Bayesian inference in order to infer the causative drug.

FIG. 9(c) shows a flowchart of a script for, when performing MRI, performing a pre-check in accordance with a label "MRI" and a link to a knowledge entry "MRI" in a tree structure of knowledge "test," in a knowledge entry attribute category <test> in a knowledge entry "disk herniation" in the tree structure of knowledge "disease name."

Including the reference strength and reference characteristics management means that manages the script to be performed when making reference as described above is useful in performing Bayesian inference or leads to elimination of check errors, resulting in an improvement in medical safety. Also, by configuring the reference characteristics management means to be able to change the reference strength in accordance with the observation frequency in a case, Bayesian inference or the like can be performed more precisely in accordance with the situation.

For example, when describing "fever" in <symptoms> of one patient, the reference characteristics management means may be used to manage the polarity of "presence/absence" of fever in a reference link to a knowledge entry "fever" in the tree structure of knowledge "symptoms/findings." Also, a reference link from the knowledge entry "fever" to the medical record of this patient may be placed simultaneously. Thus, an inquiry about the ratio between patients with fever and all patients, or a request for a list of patients with fever can be answered easily.

While the tree-structure-of-knowledge group shown in FIG. 3 relate to medical care, there are also other numerous fields in which knowledge should be described, such as art and industry.

A tree structure of knowledge name is required to be unique so that it does not overlap other tree structure of knowledge names. If the same tree structure of knowledge name is used in an unrelated other field, a troublesome problem occurs.

Figure 10:
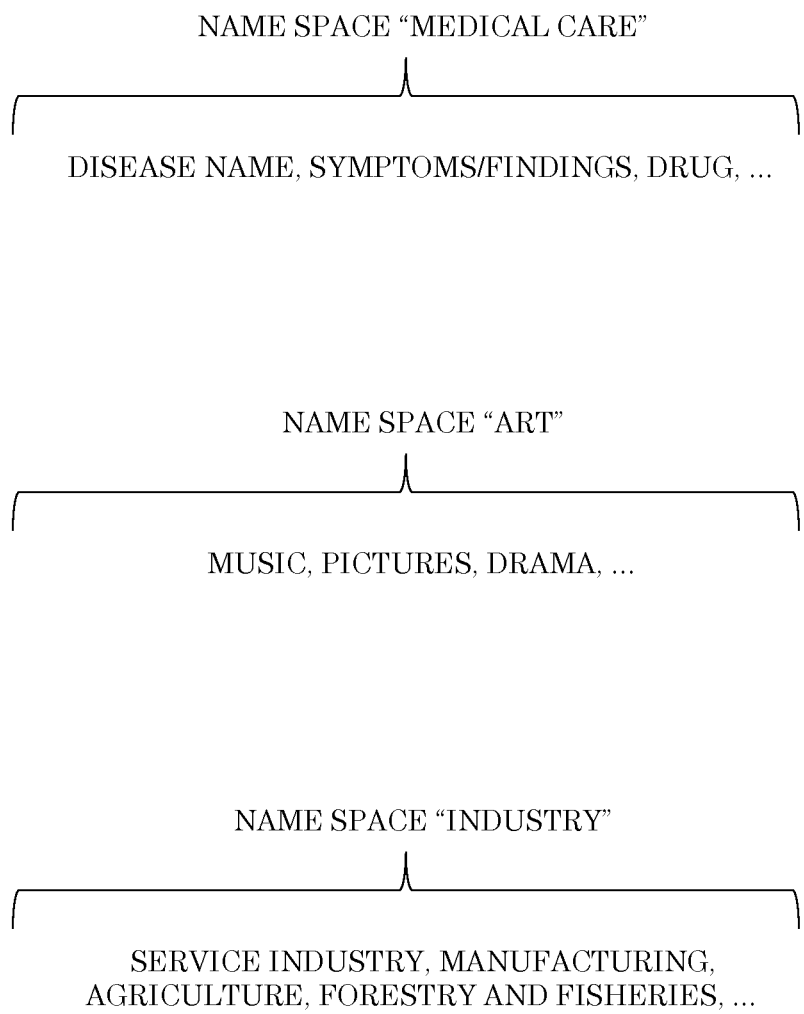
FIG. 10 is a diagram showing name space management.

To avoid this problem, a name space is set for each field, as shown in FIG. 10. Thus, a tree structure of knowledge name becomes name space+tree structure of knowledge name and thus is completely separated from tree structure of knowledge names in other fields. FIG. 11 shows an example in which name space IDs and name space names are managed in the form of a master table (name space management means). By adding name space IDs as the first column of FIG. 4, 6, or 8 as necessary, large-scale knowledge can be managed without confusion.

Figure 12:
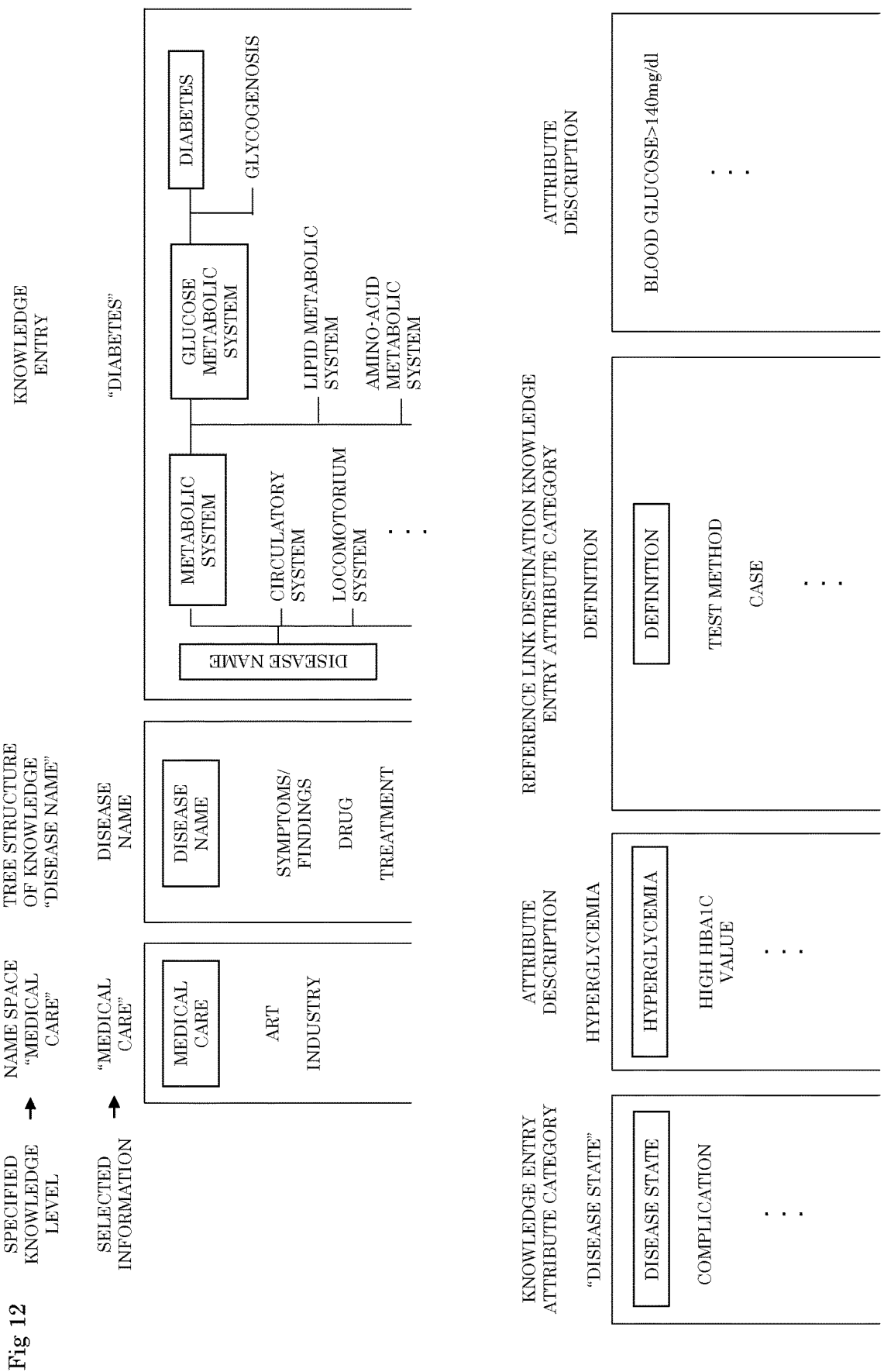
FIG. 12 is a diagram showing an example screen configuration of knowledge view means.

FIG. 12 shows an example of knowledge view means.

First, "medical care" is selected from a list of name spaces forming the first column from the left.

Thus, the names of group of tree structures of knowledge belonging to the name space "medical care" are listed in the second column. When a tree structure of knowledge "disease name" is selected, a list of major categories, such as "metabolic system" and "circulatory system," is first shown. When "metabolic system" is selected, a list of medium categories, such as "glucose metabolic system" and "lipid metabolic system," is shown thereunder.

When "glucose metabolic system" is selected, minor categories, such as "diabetes" and "glycogenosis," are listed thereunder.

When "diabetes" is selected, knowledge entry attribute categories, such as <disease state> and <complication>, are shown.

When <disease state> is selected, reference links, such as "hyperglycemia" and "high HbA1c value," which are attribute descriptions included in <disease state>, are shown.

When "hyperglycemia" is selected, there are shown attribute categories <definition>, <test method>, and the like in the knowledge entry "hyperglycemia" in the tree structure of knowledge "symptoms/findings," which is the reference link destination.

When <definition> is selected, details of this knowledge entry attribute category are shown.

While it is useful to take views manually as shown in FIG. 20, it is more useful to make an inquiry about search or the like to the knowledge management system, to perform a process such as a set operation or logical operation on the search result, and to display the result or download it into a file.

It is efficient to describe a series of inquiry steps in the form of a script or the like and to sequentially automatically process the steps (knowledge inquiry receiving means and knowledge inquiry response means).

The knowledge management system of the present invention is assumed to be constructed on cloud computing.

However, some companies or hospitals are operating a knowledge management system without connecting to the Web, for security reasons. In such a case, by providing such an on-premises knowledge management system with knowledge export means that creates a knowledge management subset by extracting any portions of the name spaces, tree structures of knowledge, knowledge entries, entry attribute descriptions, and parent-child relationship links forming the knowledge management system and exports the knowledge management subset to another knowledge management system and knowledge import means that imports the knowledge management subset extracted by the knowledge export means or a knowledge management subset from a separately constructed knowledge management system and integrates the name spaces, tree structures of knowledge, knowledge entries, entry attribute descriptions, and parent-child relationships into the on-premises knowledge management system for reconfiguration, part or all of the knowledge management system constructed on cloud computing may be incorporated into the on-premises knowledge management system.

If one company constructs an excellent knowledge management system on its own and another company wants to purchase it, part or all of the knowledge management system of the present invention may be transferred to the excellent knowledge management system in accordance with a similar procedure.

The knowledge management system handles an enormous amount of information and therefore requires cooperation of many persons to create information.

It is indispensable to set, on persons involved, the authorities to perform creation, edit, deletion, reference, and the like of name spaces, tree structures of knowledge, knowledge entries, knowledge entry attribute categories, knowledge entry attribute descriptions, and parent-child relationship links in accordance with the authorities or skills of the persons (user authority management means).

This can prevent a user who poorly understands the knowledge management system from breaking it. Also, by limiting the range of knowledge referred to by a user, knowledge that should be secret can be kept secret.

Database types on which the knowledge management system of the present invention can be implemented include graph database such as Neo4j, relational database (RDB), which has often been used, key-value store (KVS), which has recently attracted attention as a method to process big data, and the like.

Any database type may be used but has advantages and disadvantages.

First, Neo4J is good at setting and displaying a network graph relationship, but cannot necessarily perform a large-scale process at high speed and is not suitable for large knowledge management systems.

The knowledge management system of the present invention can be implemented on an RDB by making a parent-child relationship link or knowledge entry attribute description in each row of a relation under the management of a master table consisting of name spaces, tree structures of knowledge, knowledge entries, and knowledge entry attribute categories.

An RDB provides highly flexible search, includes all query languages, including SQL, and has many conventional software assets. Accordingly, it is realistic to implement the knowledge management system on an RDB.

A KVS consists of one to several items of data (column) and a data set serving as a key. While a KVS is inferior to an RDB, which provides a wide variety of free search, it is able to perform a distributed process such as MapReduce on a large amount of data at high speed.

If electronic health records or the like are actually used, an enormous number of cases are shortly listed in <case> of FIG. 5, <case> of "hyperglycemia" in the tree structure of knowledge "symptoms/findings." or the like. The frequency distribution of one attribute is easily obtained even if any method is used. However, if the frequency of a case consisting of multiple factors, for example, the frequency of a case in which "a diabetes patient has HbA1c exceeding 10 and urine protein of 2+ or more," is obtained from large-scale case data, the processing ability of the RDB may be exceeded. In such a case, it is necessary to perform a set operation among a list of diabetes patients, a list of patients of HbA1c>10, and a list of patients of urine protein>2+. In such a case, it is extremely useful to perform a distributed process using MapReduce of a KVS.

In the knowledge management system of the present invention, the knowledge entries form a hierarchical structure. Thus, for example, when searching for a list of patients with "fever," the search range can be extended to lists of patients with "remittent fever," "continued fever," and the like, which are subordinate concepts of "fever," as necessary.

While the knowledge management system of the present invention may be implemented on any type of database as described above, combined implementation, such as that in which the fundamental portion of the knowledge management system is processed on an RDB and a case list or the like is processed on a KVS, would be most useful.

Although the authorities to access the knowledge management system are set on users using the user authority management means, this is not enough. There are cases in which followers of conflicting theories repeatedly overwrite each other's writes to deny them. A solution to such a case is use of search scope management means that removes the writes of one particular user from the search target to prevent another user from viewing them. Thus, a peaceful solution is possible.

While "chest pain" is more likely to be diagnosed as myocardial infarction in a heart disease hospital, it is more likely to be diagnosed as rib fracture in an orthopedic outpatient department. As seen above, the prior distribution of the incidence of a symptom or finding often varies among clinical departments or the like. In such a case, it is useful to set a search scope in which similar clinical departments, medical institution types, and areas are combined.

While an embodiment has been described, the specific configuration of the present invention is not limited to the embodiment. Design changes and the like are also included in the present invention without departing from the spirit and scope of the invention.

For example, while the present invention has been discussed using medical care as an example in the present application, it can also be discussed using education, personnel affairs, or the like as an example. The criteria for classifying tree structures of knowledge, knowledge entries, and the like, settings of knowledge entry attribute categories, and the like must be carefully defined by an experienced designer. The classification criteria of the present application are only illustrative. Once the classification criteria are defined, subsequent fluctuations in the descriptions are minimized.

The invention claimed is:

1. A knowledge management system comprising:
   knowledge entry management means configured to manage at least one knowledge entry in recording and managing medical knowledge;
   knowledge entry attribute description management means configured to record and manage an attribute description about the at least one knowledge entry, wherein a term used in the attribute description is another knowledge entry or an attribute description of the other knowledge entry defining or describing the term and wherein a reference link to the other knowledge entry or the attribute description of the other knowledge entry is available;
   reference term-using document creation means configured to create a document in which the knowledge entry managed by the knowledge entry attribute description management means is used as a term and that holds a reference link to the knowledge entry; and
   reference characteristics management means configured to manage a pre-check script to be executed when making reference,
   wherein the reference characteristics management means is configured to be able to change strength of the reference in accordance with an observation frequency in a case.

2. The knowledge management system of claim 1, comprising knowledge entry attribute category management means configured to manage the knowledge entry attribute description such that the knowledge entry attribute description is classified into a category.

3. The knowledge management system of claim 1, comprising:
   tree-structure-of-knowledge group management means configured to manage at least one tree structure of knowledge;
   knowledge entry management means configured to manage at least one knowledge entry present in each of the at least one tree structure of knowledge, wherein each of the at least one knowledge entry comprises a knowledge entry attribute description describing an attribute about the knowledge entry and a knowledge entry parent-child relationship link describing a parent-child relationship with another knowledge entry of the at least one tree structure of knowledge; and
   tree-shaped knowledge management means in which the knowledge entry attribute description comprises a term defined by a knowledge entry belonging to a different or identical tree structure of knowledge or an entry attribute description of the knowledge entry, and a reference link to the term.

4. The knowledge management system of claim 3, comprising knowledge entry attribute description inheritance means configured to inherit an entry attribute description of a parent knowledge entry as an entry attribute description of a child knowledge entry in the parent-child relationship.

5. The knowledge management system of claim 1, comprising external document reference means configured to refer to an external document related to an entry attribute description.

6. The knowledge management system of claim 3, comprising name space management means configured to manage the at least one tree structure of knowledge such that the at least one tree structure of knowledge is classified into a name space.

7. The knowledge management system of claim 1, comprising knowledge export means configured to create a knowledge management subset by extracting any portions of a name space, a tree structure of knowledge, a knowledge entry, an entry attribute description, and a parent-child relationship link and to export the knowledge management subset to another knowledge management system.

8. The knowledge management system of claim 7, comprising knowledge import means configured to import the knowledge management subset extracted by the knowledge export means or a knowledge management subset from a separately constructed knowledge management system and to reconfigure a name space, a tree structure of knowledge, a knowledge entry, an entry attribute description, and a parent-child relationship link.

9. The knowledge management system of claim 6, comprising user authority management means configured to manage user-specific authorities to perform functions of creating, editing, deleting, and referring to the name space, the tree structure of knowledge, the knowledge entry, the knowledge entry attribute category, the knowledge entry attribute description, and the parent-child relationship link.

10. The knowledge management system of claim 3, comprising knowledge view means configured to allow a user to view the parent-child relationship between the at least one knowledge entry and the other knowledge entry or the knowledge attribute description of the at least one knowledge entry.

11. The knowledge management system of claim 1, comprising knowledge inquiry receiving means configured to receive an inquiry about recorded or managed information and knowledge inquiry response means configured to respond to the inquiry.

12. The knowledge management system of claim 10, comprising search scope management means configured to manage users who have created the name space, the tree structure of knowledge, the knowledge entry, the entry attribute description, and the parent-child relationship link and to exclude a portion of a knowledge management system created by a specific user or user group from a search target range of the view or the knowledge inquiry or conversely handle only a portion of a knowledge management system created by a specific user or user group as the search target range of the view or the knowledge inquiry.

* * * * *